US 9,525,930 B2

(12) United States Patent
Parkins

(10) Patent No.: US 9,525,930 B2
(45) Date of Patent: *Dec. 20, 2016

(54) MAGNETIC FIELD ANTENNA

(71) Applicant: Red Tail Hawk Corporation, Ithaca, NY (US)

(72) Inventor: John W. Parkins, Ithaca, NY (US)

(73) Assignee: Red Tail Hawk Corporation, Philadelphia, PA (US)

(*) Notice: Subject to any disclaimer, the term of this patent is extended or adjusted under 35 U.S.C. 154(b) by 282 days.

This patent is subject to a terminal disclaimer.

(21) Appl. No.: 14/191,783

(22) Filed: Feb. 27, 2014

(65) Prior Publication Data
US 2014/0177863 A1 Jun. 26, 2014

Related U.S. Application Data

(63) Continuation-in-part of application No. 12/832,363, filed on Jul. 8, 2010, now Pat. No. 8,693,720, which is a continuation-in-part of application No. 11/837,129, filed on Aug. 10, 2007, now Pat. No. 8,688,036.

(60) Provisional application No. 61/224,531, filed on Jul. 10, 2009, provisional application No. 60/824,091, filed on Aug. 31, 2006.

(51) Int. Cl.
H04R 1/10 (2006.01)
H01Q 1/27 (2006.01)
H01Q 7/08 (2006.01)
A61F 11/08 (2006.01)
H04M 1/05 (2006.01)

(52) U.S. Cl.
CPC ............ *H04R 1/1091* (2013.01); *H01Q 1/273* (2013.01); *H01Q 7/08* (2013.01); *A61F 11/08* (2013.01); *H04M 1/05* (2013.01)

(58) Field of Classification Search
CPC ... H04R 1/1091; H04R 1/1041; H04R 1/1075; H04R 2209/041; A61F 11/08; H04M 1/05; H04M 1/215; H04M 1/6066
USPC ........................ 381/312, 315, 320, 332, 424, 74,381/326–330; 455/41.1; 379/52
See application file for complete search history.

(56) References Cited

U.S. PATENT DOCUMENTS

| 2,048,604 A | 7/1936 | Finch |
| 2,268,665 A | 1/1942 | Loewe |
| 2,530,621 A | 11/1950 | Lybarger et al. |
| 3,125,646 A | 3/1964 | Lewis |
| 3,322,897 A | 5/1967 | Vozeolas et al. |
| 3,752,939 A | 8/1973 | Bartz |
| 4,150,262 A | 4/1979 | Ono |

(Continued)

FOREIGN PATENT DOCUMENTS

| DE | 3508830 A1 | 9/1986 |
| DE | 3826294 A1 | 2/1990 |
| WO | 2006042298 A2 | 4/2006 |

OTHER PUBLICATIONS

SJSU "Electromagnetic Induction", http://www.physics.sjsu.edu/becker/physics51/induction.htm; pp. 1-23; Jan. 2007.

(Continued)

Primary Examiner — David Ton
(74) Attorney, Agent, or Firm — Brown & Michaels, PC

(57) ABSTRACT

A magnetic field antenna that provides high efficiency and a compact form factor. Electromagnetic shielding of electrical components used in the antenna is provided, and one embodiment of the invention is a wireless battery-free communications earplug.

25 Claims, 8 Drawing Sheets

(56) References Cited

U.S. PATENT DOCUMENTS

| | | | |
|---|---|---|---|
| 4,957,478 | A | 9/1990 | Maniglia |
| 4,972,491 | A | 11/1990 | Wilcox, Jr. |
| 5,073,947 | A | 12/1991 | Reddemann et al. |
| 5,343,532 | A | 8/1994 | Shugart, III |
| 5,396,563 | A | 3/1995 | Yoshimi |
| 5,420,930 | A | 5/1995 | Shugart, III |
| 5,701,348 | A | 12/1997 | Shennib et al. |
| 5,796,821 | A | 8/1998 | Crouch et al. |
| 6,012,812 | A | 1/2000 | Rickards |
| 6,078,675 | A | 6/2000 | Bowen-Nielsen et al. |
| 6,208,740 | B1 | 3/2001 | Grever |
| 6,438,245 | B1 | 8/2002 | Taenzer et al. |
| 6,694,034 | B2 | 2/2004 | Julstrom et al. |
| 6,823,171 | B1 | 11/2004 | Kaario |
| 6,925,179 | B2 | 8/2005 | Waldron et al. |
| 7,206,426 | B1 | 4/2007 | Julstrom et al. |
| 7,426,279 | B2 | 9/2008 | Cochran et al. |
| 7,680,292 | B2 * | 3/2010 | Warren ............... H04R 1/1016 381/322 |
| 8,116,494 | B2 | 2/2012 | Rass |
| 8,693,720 | B2 * | 4/2014 | Parkins ............... H04R 1/1091 381/315 |
| 2002/0061113 | A1 | 5/2002 | van Halteren et al. |
| 2002/0141545 | A1 | 10/2002 | Segovia |
| 2003/0031339 | A1 | 2/2003 | Marshall et al. |
| 2003/0219135 | A1 | 11/2003 | Morimoto |
| 2004/0151334 | A1 | 8/2004 | Vaudrey et al. |
| 2004/0258261 | A1 | 12/2004 | Cochran et al. |
| 2005/0018859 | A1 | 1/2005 | Bucchholz |
| 2005/0078848 | A1 | 4/2005 | Hlibowicki |
| 2005/0094830 | A1 | 5/2005 | Stanley |
| 2005/0245213 | A1 | 11/2005 | Hirano et al. |
| 2005/0260953 | A1 | 11/2005 | Lefler et al. |
| 2006/0013420 | A1 | 1/2006 | Sacha |
| 2006/0269088 | A1 | 11/2006 | Julstrom et al. |
| 2007/0041602 | A1 | 2/2007 | Killion |
| 2007/0041606 | A1 | 2/2007 | Sheppard |
| 2007/0149261 | A1 | 6/2007 | Huddart |
| 2007/0153444 | A1 | 7/2007 | Groh et al. |
| 2008/0025524 | A1 | 1/2008 | Vaudrey et al. |
| 2008/0132193 | A1 | 6/2008 | Petrovic et al. |
| 2009/0041285 | A1 | 2/2009 | Parkins et al. |
| 2009/0143097 | A1 | 6/2009 | Wilson |
| 2010/0014700 | A1 * | 1/2010 | Zhou .................... H04R 11/02 381/380 |
| 2010/0016827 | A1 | 1/2010 | Hunter et al. |
| 2010/0278371 | A1 | 11/2010 | Hanada |
| 2010/0296667 | A1 | 11/2010 | Parkins |
| 2011/0081936 | A1 | 4/2011 | Haim et al. |
| 2011/0103605 | A1 | 5/2011 | Killion et al. |
| 2011/0130622 | A1 | 6/2011 | Ilberg |
| 2012/0021704 | A1 | 1/2012 | Chan et al. |
| 2012/0275638 | A1 | 11/2012 | Chang |
| 2012/0322378 | A1 | 12/2012 | Tai |
| 2013/0244722 | A1 | 9/2013 | Rousu et al. |
| 2014/0087659 | A1 | 3/2014 | Parkins |
| 2014/0295909 | A1 | 10/2014 | Ouchi et al. |

OTHER PUBLICATIONS

James et al. "Protecting Crew Members against Military Vehicle Noise." Presented at the RTO AVT Symposium and published in RTO-MP-AVT-110; pp. 1-18; Oct. 2004.
Knowles Acoustic ED Series Speaker Specification. Dec. 2003.
Viking Chip Common Mode Choke-CM Series. Apr. 2006.
Van Wiljngaarden et al. "Development of the Wireless "Communications Earplug" for application in Military Aviation" J. Audio Eng. Soc., vol. 48, No. 6, Jun. 2000.

* cited by examiner

MAGNETIC FIELD ANTENNA

REFERENCE TO RELATED APPLICATIONS

This application is a continuation-in-part of co-pending U.S. application Ser. No. 12/832,363, published as publication number US 2010/0296667, entitled "Wireless Earplug with Improved Sensitivity and Form Factor", filed Jul. 8, 2010, which claimed the benefit of Provisional Application No. 61/224,531, filed Jul. 10, 2009, entitled "Wireless Earplug with Improved Sensitivity and Form Factor", and was a continuation-in-part of U.S. application Ser. No. 11/837,129, published as publication number US 2009/0041285, entitled "Wireless Communications Headset System Employing a Loop Transmitter That Fits Around the Pinna", filed Aug. 10, 2007, which claimed the benefit of Provisional Application No. 60/824,091, filed Aug. 31, 2006, entitled "Wireless Communications System Employing a Loop Transmitter That Fits Around The Pinna". The aforementioned applications are hereby incorporated herein by reference.

BACKGROUND OF THE INVENTION

Field of the Invention

This invention relates to the field of wireless communications earplugs, magnetic field antennas and radio frequency identification devices.

Description of Related Art

Aircraft radios and intercoms typically provide electrical audio outputs for connecting aviation headsets. The audio signal from an aircraft radio, provided as an electrical signal at an audio output, can directly drive an aviation headset that incorporates headset speakers with enough sensitivity to provide clear acoustic audio communications.

Published applications US 2009/0041285 and US 2010/0296667, of which this application is a continuation-in-part, describe components of a system that can be used for wireless earplug communications. In one embodiment described in US 2009/0041285, a magnetic field antenna (MFA) may be used as a battery-free wireless communications earplug in which only passive electrical components are employed. The sensitivity of the antenna achieves adequate sound pressure level (SPL) and perceived acoustic volume with typical aircraft radios, and the small earplug size provides a comfortable earplug.

A pair of magnetic loop transmitters, such as a loop transmitter that fits around the pinna of the user as seen in at least FIG. 12 of US 2009/0041285, can be installed in a headset instead of the speakers, or used in conjunction with the speakers. The audio electrical signal output from the aircraft radio can drive these loop transmitters in a headset and be received by the battery-free communications earplugs of US 2009/0041285 and US 2010/0296667 with enough system sensitivity to drive the speakers of the earplugs to achieve high enough SPL for clear speech communications and high speech intelligibility, while providing an earplug design that fits in a human ear.

Moreover, electromagnetic shielding of electrical components used in wireless earplugs is important to prevent pickup of spurious fields. However, the antenna must be small enough to fit comfortably in the human ear. Large communications earplugs tend to be uncomfortable because they put pressure on the ear. Moreover, a large earplug may interfere with a headset earcup when the earplug and headset are worn together to provide "double hearing protection". A higher sensitivity MFA device can achieve the same sensitivity as a lower sensitivity MFA but in a smaller package size.

It is known in the art that an antenna coil can be constructed using a helical coil of wire with at least one turn. According to Faraday's Law, also well-known in the art, a time-varying magnetic field passing through the inner region of a coil will produce a voltage on the ends of the coil proportional to the time derivative of the magnetic flux through the turns. The magnetic flux through a coil is proportional to the density of magnetic field lines passing through it. When an antenna coil is used to generate a voltage from a magnetic field, it is called a receiver coil. When an antenna coil is used to generate a magnetic field by applying a voltage or current to the coil, it is called a transmitter coil.

Electromagnetic waves impinging on electrical components can produce undesired voltages and currents that cause undesired effects. The source of the electromagnetic waves may be a remote communications transmitter, the transmitter antenna of an embodiment of the invention or they may be stray electromagnetic waves generated by other equipment. It is undesirable for the electrical components used within the antenna to generate voltages from external fields in an unpredictable way. Even connection wires benefit from electromagnetic shielding. In particular, electret microphones are sensitive to electromagnetic fields, and this is a known problem in the art.

SUMMARY OF THE INVENTION

An embodiment of the MFA described herein has an antenna coil for sensing a magnetic field and/or creating a magnetic field, a magnetic core within the coil, a magnetic core extension used to redirect magnetic field lines through the magnetic core and antenna coil, any electrical components coupled to the antenna coil, and any magnetic material used as a magnetic shunt to at least partially shield an electrical component coupled to the antenna coil. The MFA may be housed within a suitable structure for particular applications. For example, an embodiment of the invention can be enclosed at least partially within an earshell to create a wireless communications earplug, among other applications.

In embodiments of the invention, the coil core and core extension together can form an antenna body where the coil core and core extension comprise multiple parts or a single mechanical part.

In one embodiment of the invention, a microphone is used in an MFA earplug transmitter to sense SPLs in the user's ear and transmit SPL levels to a remote receiver for noise dosimetry purposes. Any shielding that shunts the electromagnetic field away from the microphone in this embodiment is highly desirable.

In accordance with a preferred embodiment of the invention, at least a portion of the antenna body of the MFA is used as a continuation of the magnetic core for an antenna coil, thus directing a greater number of magnetic field lines through the antenna coil. In a preferred embodiment, the antenna body of the MFA also provides a magnetic shunt around at least one electrical component electrically coupled to the antenna coil to provide at least partial magnetic shielding of the electrical component.

DETAILED DESCRIPTION OF THE INVENTION

It should be noted here that for explanatory purposes the figures herein include indications of unperturbed field lines, redirected magnetic field lines and optimal orientations of the MFA relative to the field. The field lines and orientations are provided for illustrative purposes and should not be taken to be exact representations of optimal orientations and magnetic field line paths.

Figure 1:
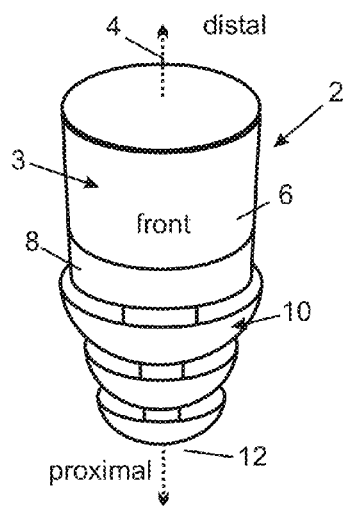
FIG. 1 is a view of an embodiment of the invention as a wireless communications earplug.

FIG. 1 shows a three-dimensional drawing of an embodiment of the invention: a battery-free wireless communications earplug 2. The exterior geometry of the communications earplug 2 embodiment of the invention is symmetric about an earplug axis 4. The proximal end of the communications earplug 2 is the end that is closest to the eardrum when the communications earplug 2 is properly inserted in an ear. The distal end is the end farthest from the eardrum. This embodiment of the invention incorporates an outer surface 3 comprising a cover 6 and base 8.

This embodiment is sized to fit in a human ear with an eartip 10 that at least partially acoustically seals the communications earplug 2 to the walls of ear canals (not shown) to provide acoustic noise attenuation. Eartips can be universal fitting—such as the triple-flanged elastomer eartip 10 shown in FIG. 1, single flanged eartips, and foam eartips among others types. An eartip can also be custom molded to form fit to an individual's ear canal and/or ear concha geometry. These custom eartips are often made of silicon or plastic among other materials. Eartips could incorporate impregnated magnetic material. Sound generated by a speaker within the communications earplug exits the eartip 10 through an eartip outlet 12.

Figure 2:
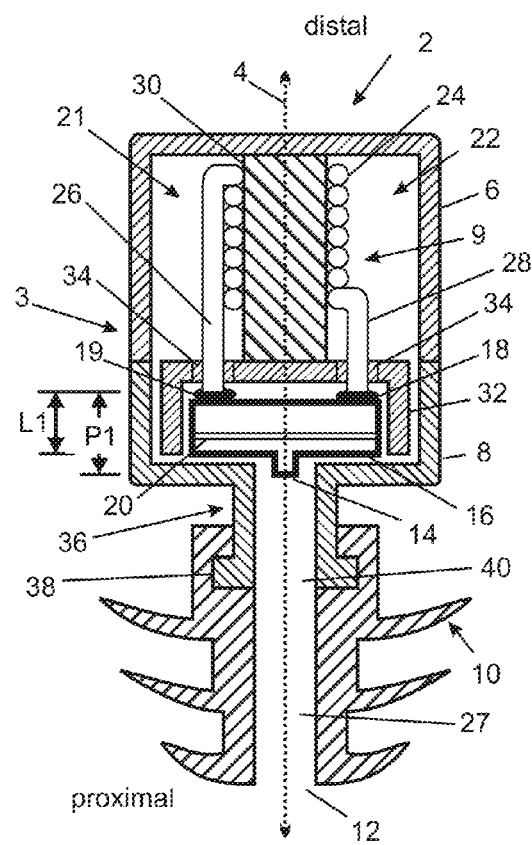
FIG. 2 is a cross-sectional frontal view of the embodiment shown in FIG. 1 along the axis of symmetry of the earplug.

FIG. 2 shows a frontal view cross section of the communications earplug of FIG. 1 along the earplug axis 4. Within the interior of the communications earplug 2 is a receiver 9 comprising an antenna coil 21 of wire with a first turn 24, coil ends 26 and 28, and magnetic core 30. The coil ends, 26 and 28, pass through perforations 34 of a speaker case 32 and are electrically coupled to a speaker 16 with speaker diaphragm 20 at speaker terminals 18 and 19. Note that the antenna coil 21 is not drawn with hatching in the figures herein to make the drawings less cluttered and easier to comprehend. The magnetic core 30 is in close proximity to the top surface of the speaker case 32, and preferably touching.

The magnetic material of a core and core extension increases the voltage sensitivity of a receiver coil by redirecting magnetic field lines through the inner region of the coil. Magnetic material has a lower reluctance compared to air, and a given magnetic field line takes the closed path of lowest reluctance to complete its path from the transmitter out to the environment and back around the transmitter. (Note that electrical resistance in electrical circuits is analogous to magnetic reluctance in magnetic circuits.) Small gaps, approximately up to 0.03 inch, of non-magnetic material between a core and core extension may be tolerated in some applications, but non-magnetic gaps are undesirable because they reduce sensitivity of the antenna.

As an example, when a receiver coil of outer diameter 0.30 inch is wrapped around a magnetic core of length 0.32 inch, which is also used as a bobbin for wrapping the coil, an open circuit voltage is measured at the coil ends. If the coil geometry remains the same, but the magnetic core is doubled in length, the voltage may be increased by 50 percent. In this way, the voltage sensitivity of the receiver has increased significantly.

If one end of the same receiver coil with magnetic core is placed on top of a rectangular enclosure of 0.16 inch height, 0.28 inch width and 0.39 inch length made from 0.010 inch thick magnetic metal, the coil voltage may be increased by 40%. This is also a significant sensitivity increase. Magnetic enclosures of this approximate size can be used to house and shield electrical components such as speakers, microphones, accelerometers, passive electronic circuits, wires, circuit boards, battery-powered systems, batteries, digital circuits, memory chips, digital signal processors, analog-to-digital converters, digital-to-analog converters and many other electrical devices.

The speaker 16 has a speaker outlet 14 that allows sound generated by the moving speaker diaphragm 20 to travel through an eartip adapter 36 via a sound channel 40. In this embodiment of the invention, the interior parts are symmetric about the earplug axis 4 except for the coil ends 26 and 28, the helical geometry of the antenna coil 21, the speaker terminals 18 and 19 and perforations 34.

An eartip adapter is a mechanical part with two ends that provides at least a mechanical means for attaching an eartip and a sound channel within its interior for acoustically coupling sound from one end of the eartip adapter to the other end. The barb 38 shown in FIG. 2 is cylindrical with a rectangular cross section, in this embodiment, but could have a screw-thread shape for threading on an eartip, or employ a plain cylindrical shaft or other geometries as seen in commercially available eartip adapter designs. The mechanical means for attaching an eartip may also be a fitting with no barb where the eartip is secured using adhesive or other means.

The eartip has a sound channel 27 through its center to allow sound to travel from the speaker outlet 14 through the eartip adapter sound channel 40 and through the eartip sound channel 27 out the eartip outlet 12 into the ear canal to be heard by the user. Eartip adapters can be used with other acoustical components that require sound coupling such as microphones.

In FIG. 2, length P1 corresponds to the length along the earplug axis 4 of a coupled electrical component, the speaker 16 in this embodiment. The speaker case 32 has a region with length L1 that overlaps the length P1 along the earplug axis 4. The length L1 in this embodiment is shorter than P1 because the speaker outlet 14 protrudes below the speaker case 32.

Figure 3:
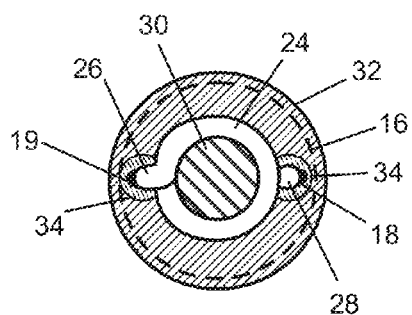
FIG. 3 is a view of the embodiment of the invention from FIG. 1 looking into the distal end of the earplug along the axis of symmetry when the eartip, earplug cover and base have been removed.

FIG. 3 shows a view of the communications earplug 2 from FIG. 1 and FIG. 2 looking into the distal end of the communications earplug 2 with the eartip 10, cover 6 and base 8 removed. From this view, the first turn 24 of the antenna coil 21 can be seen wrapped around the magnetic core 30. The outline of the speaker 16 is indicated with a dashed line.

Figure 4A:
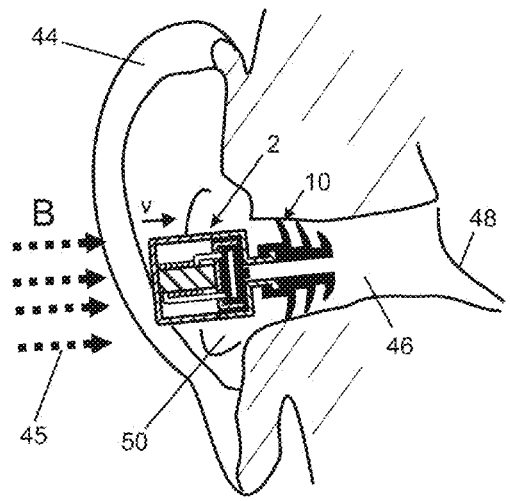
FIG. 4a is a cross-sectional view of the embodiment of the invention shown in FIG. 1 in a human ear.
Figure 4B:
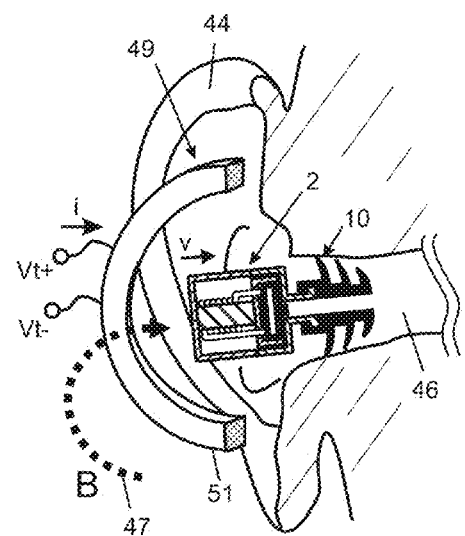
FIG. 4b is a cross-sectional view of an embodiment of the invention employing a circular transmitter coil.

FIGS. 4a and 4b show a cross-sectional view of the communications earplug 2 with eartip 10 inserted in a human ear canal 46 as it is intended to be worn. The eartip 10 faces a human eardrum 48. The eartip generally creates an acoustic seal with the ear canal 46. In this embodiment, the outer surface of the earplug 3 fits within the concha 50 region of the user while the eartip adapter 36 and eartip 10 fit in the ear canal. A pinna 44 is also shown in FIGS. 4a-4b.

A magnetic field B is used to provide communications information to the user. The magnetic field B direction, at a given point in time, is indicated by field vector v. The magnetic field B may be of oscillatory, pulsed or other time-varying natures. Non-time-varying static fields are ineffective because the antenna coil 21 only responds to the time-derivative of the field.

In the field shown in FIG. 4a, the magnetic field B is generated by a source relatively distant from the communications earplug 2, and the field lines 45 are shown as straight lines because the radius of curvature of the field lines is very large.

FIG. 4b is a cross-sectional view of an embodiment of the invention employing a circular transmitter coil 49 positioned adjacent to a pinna 44. The transmitter coil 49 comprises at least one turn of an electrical conductor. A voltage is applied across transmitter ends Vt+ and Vt−, which generates current i and magnetic field B through the inner area of the transmitter coil 49.

In this embodiment, the transmitter coil 49 is positioned in close proximity to the communications earplug 2. The transmitter coil 49 can be placed within a headset earcup or helmet or embedded in a wall or headrest or other apparatus. The transmitter coil 49 in this embodiment is enclosed in a plastic carrier 51.

Figure 5:
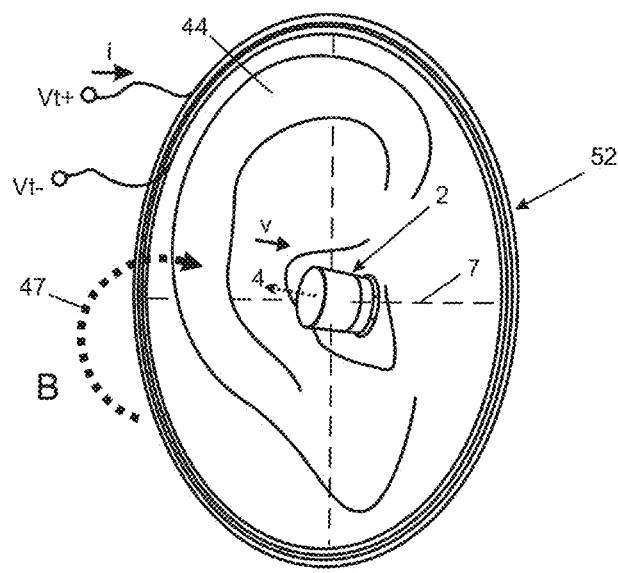
FIG. 5 is a view of the embodiment of the invention shown in FIG. 1 in a human ear along with a loop transmitter sized to fit around the pinna.

FIG. 5 shows a view of the communications earplug 2 as worn on a human ear with a loop transmitter 52 sized to fit around the pinna 44. The loop transmitter 52 comprises at least one turn of electrically conductive material. When voltage is applied across transmitter coil ends Vt+ and Vt−, current i flows through the turns of the loop transmitter 52 and creates magnetic field B. The magnetic field B in this case has many curved field lines that circulate through the inner area of the loop transmitter 52 indicated by a single field line 47. Near the center of the loop transmitter, the field vector v points in the direction generally along the earplug axis 4. This earplug 2 orientation with respect to the magnetic field B is an orientation that yields high sensitivity because the magnetic field B passes through the inner region of the antenna coil 21.

The loop transmitter 52 that fits around the pinna has the significant benefit compared to other loop geometries in that it will not mechanically interfere with the communications earplug 2 or pinna 44, because the loop transmitter 52 has a large open center, in this embodiment. The loop transmitter 52 can be placed within a headset earcup or helmet or embedded in a wall or headrest or other apparatus. Because the loop transmitter 52 can be worn around the pinna 44 and has an open center, it can be placed close to the communications earplug 2 so that the communications earplug 2 overlaps a loop transmitter 52 geometry plane 7, indicated by perpendicular dashed lines. This improves the sensitivity of the system, compared to loop transmitters worn adjacent to the pinna 44 or on the ear, because the magnetic field B strength diminishes as the separation between the geometry plane 7 of the loop transmitter 52 and communications earplug 2 increases.

Figure 6:
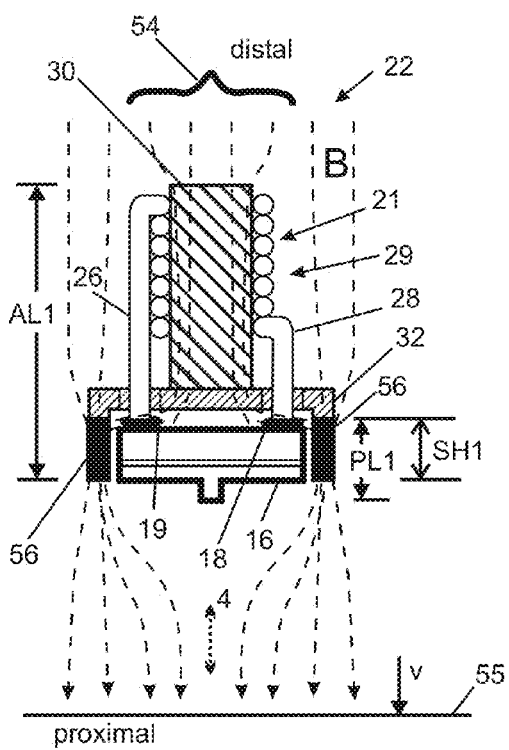
FIG. 6 is a cross-sectional view of the embodiment of the invention shown in FIG. 1 showing an embodiment of a magnetic field antenna in a magnetic field illustrating how magnetic field lines are redirected due to the magnetic material in the magnetic field antenna.

FIG. 6 shows an MFA 22 structure from the embodiment shown in FIGS. 2-4 in the far field generated by a magnetic field transmitter. The MFA 22 is oriented in the magnetic field B to achieve maximum voltage generated at the coil ends 26 and 28 which corresponds to the maximum antenna sensitivity, which in this embodiment means the earplug axis 4 is in parallel with the field vector v.

The MFA 22 comprises an antenna body 29, the antenna coil 21, and any coupled electrical components used in the embodiment, such as the speaker 16 in this embodiment. The antenna body 29 comprises the magnetic material that significantly contributes to redirecting an ambient magnetic field B through the antenna coil 21, such as the magnetic core 30 and magnetic speaker case 32, in this embodiment.

The antenna body 29 directs magnetic field lines through the antenna coil 21 by creating a low-reluctance path through the antenna coil 21. The reluctance of magnetic material is lower than that of air, and this provides an "easier" path for the magnetic field to travel through space. To the extent that more magnetic field lines are directed through the antenna coil 21 the voltage generated at the coil ends 26 and 28 is higher and the sound generated by speaker 16 is louder. The coil-sensed field lines 54 in FIG. 6 are the magnetic field lines that pass through the antenna coil 21 and generate a voltage at the coil ends 26 and 28. Four coil-sensed field lines 54 are shown in FIG. 6, illustrating how the field lines 54 are directed through the coil.

Figure 7:
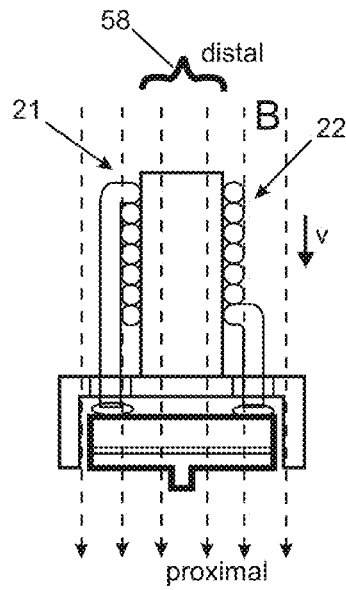
FIG. 7 shows an outline of the cross section of the embodiment of the invention shown in FIG. 6 in an unperturbed magnetic field.

Without magnetic material redirecting the magnetic field and at large distances from the magnetic field transmitter in the far field, the field lines would be uniform and straight, as shown in FIG. 7. FIG. 7 shows the outline of the MFA 22 from FIG. 6 superimposed on the unperturbed field B.

Only two coil-sensed field lines 58 are shown in this example, illustrating that fewer field lines would be sensed by the receiver coil 21 if magnetic material were not employed in the antenna body 29, thus showing the benefit of incorporating an antenna body 29 constructed of magnetic material.

The effective antenna length AL1 is the total length along the field vector v of the antenna body 29 incorporating magnetic material. The magnetic field is a far field; that is, the field lines are straight in the vicinity of the antenna body 29 when the antenna body 29 is not present, as shown in FIG. 7. In this embodiment, the effective antenna length AL1 includes the length of the magnetic core 30 and speaker case 32. A coupled electrical component length PL1 of the speaker 16 is the length of the coupled electrical component along the field vector v. Generally, longer effective antenna lengths yield a lower reluctance path for the magnetic field to travel through an antenna coil which results in a higher sensitivity MFA 22.

This embodiment of the invention incorporates a magnetic shunt 56, as seen in FIG. 6. A magnetic shunt is a section of magnetic material used in an MFA that provides a low-reluctance path adjacent to a coupled electrical component in the direction of the unperturbed field vector v that tends to redirect magnetic fields through the magnetic shunt and away from the coupled electrical component. This provides at least partial magnetic shielding of a coupled electrical component, shown in this embodiment as speaker 16.

The length of such a path along the field axis v that overlaps with the coupled electrical component effective length is the magnetic shunt length. In this embodiment, the magnetic shunt length is indicated by SH1. The magnetic shunt 56 reduces the magnetic field that travels through the coupled electrical component, providing a shielding effect and increases the effective length of the MFA body, which improves sensitivity.

Figure 8:
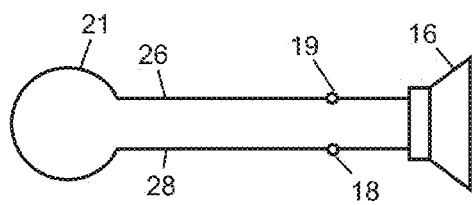
FIG. 8 shows the electrical schematic of the embodiment of the invention shown in FIGS. 1-6.

FIG. 8 shows the electrical schematic of the MFA 22 of the embodiment shown in FIG. 6. The coil ends 26 and 28 are electrically connected to the speaker terminals 18 and 19. In this way, magnetic fields sensed by the antenna coil 21 are converted to an audio electrical signal that drives the speaker 16 directly. In this embodiment, no DC voltage or DC current supply is employed, and the MFA 22 is a passive device.

When the MFA 22 is oriented in a magnetic field for maximum sensitivity, as shown in FIG. 6, a single turn of the coil 21 may be projected onto a field perpendicular plane 55. The field perpendicular plane 55 is a mathematical construct that is a surface perpendicular to the field vector v.

Figure 9:
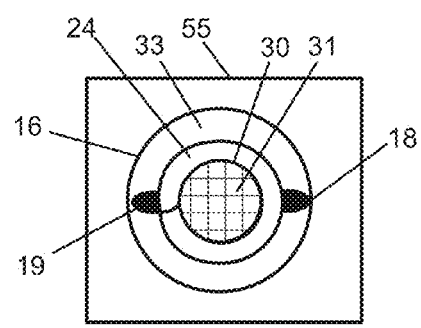
FIG. 9 shows an antenna coil and speaker of the embodiment of the invention shown in FIGS. 1-6 projected onto the perpendicular field plane.

FIG. 9 shows the field perpendicular plane 55 and the first turn 24 of the coil 21 projected onto the plane along the field vector v. FIG. 9 also shows a coupled electrical component (the speaker 16) geometry projected onto the field perpendicular plane 55 along the field vector v. The speaker terminals 18 and 19 are shown for reference.

The projected first turn 24 defines a turn projected area 31 that is, in this embodiment, the same as the cross-sectional area of the magnetic core 30. The outline of the projected speaker 16 defines a projected component area 33, which comprises the area within the outline of the projected component. The intersection of the turn projected area 31 and the projected component area 33 result in another area, which in this embodiment is equal to the first turn projected area 31.

Thus, when the MFA 22 is placed in a far field with optimal orientation with regard to sensitivity at least one turn of the coil 21 is "coincident" with a coupled electrical component of the MFA 22. This geometry results in an antenna coil 21 and at least one coupled electrical component that are generally along the magnetic field path and enables an antenna body 29 geometry that can provide a low reluctance path through an antenna coil in a small package that can yield a relatively high sensitivity and shielding of electrical components.

Figure 10:
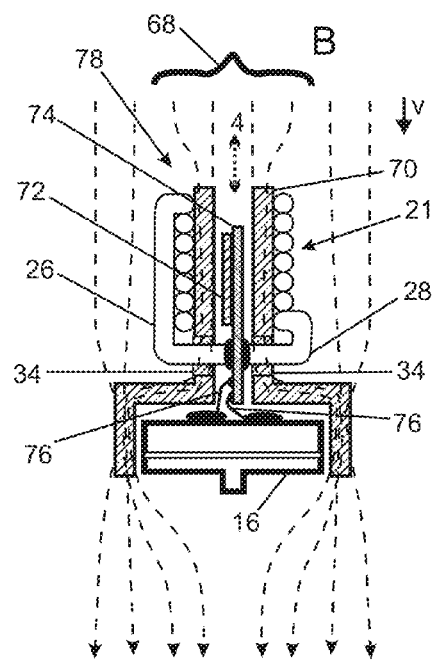
FIG. 10 shows a cross section of a preferred embodiment of the invention in a magnetic field where the antenna body comprises a single mechanical part.

FIG. 10 shows another embodiment of the invention where the magnetic core and magnetic speaker case, which is a core extension, are merged into a single part to form the antenna body 70 which is also a single part core/extension. In this embodiment, the magnetic body 70 is formed from a single piece of magnetic metal. Depending on the desired thickness of the metal, the antenna body 70 may be formed using various techniques such as spin forming, stamping, vapor deposition, electroplating, molding or other methods. The use of a single mechanical part for the antenna body 70 instead of using a separate magnetic core and speaker case can result in a mechanically stronger component. This can be important in the case of communications earplugs that could be stepped on or otherwise mechanically stressed.

The embodiment in FIG. 10 also incorporates a circuit board 74 and an electronics circuit 72. The coil ends 26 and 28 are electrically connected to the circuit board 74 by passing through perforations 34 in the antenna body 70. The speaker 16 is also connected to the circuit board 74 in this embodiment using connection wires 76.

In this embodiment, the circuit board 74 and electronics circuit 72 are well shielded within the antenna body 70 and the speaker 16 is partially shielded by shunting effects of the antenna body 70. Even though this embodiment does not incorporate a solid magnetic core like the embodiment shown in FIG. 6, this embodiment provides a similar redirection of the magnetic field through the antenna coil 21 because the magnetic material still has a much lower reluctance compared to that of air. Four coil-sensed field lines 68 are shown in FIG. 10, illustrating how the field lines 68 are directed through the coil. This embodiment of the invention can be less expensive because of the use of a single mechanical part for the antenna body 70 rather than multiple parts assembled together.

Figure 11:
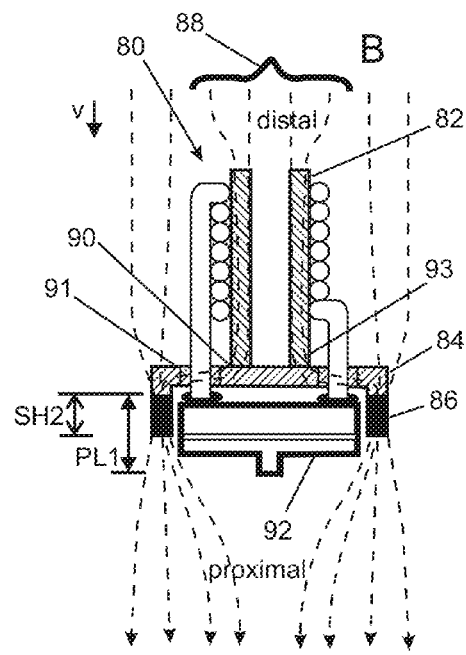
FIG. 11 shows a cross section of another embodiment of the invention in a magnetic field where the antenna body comprises two mechanical parts, where the antenna core is hollow and where the speaker and magnetic shunts are not axially symmetric.

The embodiment shown in FIG. 11 employs a hollow magnetic core 82 and a separate magnetic speaker case 84 employed in an MFA 80. A top surface 91 of the speaker case 84 is in close proximity to an end 93 of the magnetic core 82 and preferably in contact shown by the region 90.

Figure 12:
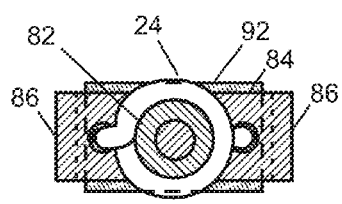
FIG. 12 shows a view of the embodiment of the invention shown in FIG. 11 looking into the distal end of the embodiment.

This embodiment does not employ a generally cylindrical geometry for a speaker 92 or speaker case 84, as seen in FIG. 12 looking into the distal end of this embodiment. The speaker 92 and speaker case 84 in this embodiment employ rectangular geometries. This embodiment employs bent magnetic shunt tabs 86, rectangular magnetic metal, extending down adjacent to the speaker 92. A coupled electrical component, the speaker 92, has an effective part length of PL1 in the direction of the field vector v when the MFA 80 is placed in a far field with maximum sensitivity orientation. An effective length herein is the length of the projection of an object onto the field vector v.

It can be seen in FIG. 11 that a magnetic shunt length SH2 is shorter than the effective part length PL1 of the speaker 92 that it is shunting; however, the magnetic shunt tabs 86 will still provide some beneficial shielding of the speaker 92 and improves the sensitivity of the MFA 80 by increasing the effective magnetic body length. Four coil-sensed field lines 88 are shown in FIG. 11, illustrating how the field lines 88 are directed through the coil.

Figure 13:
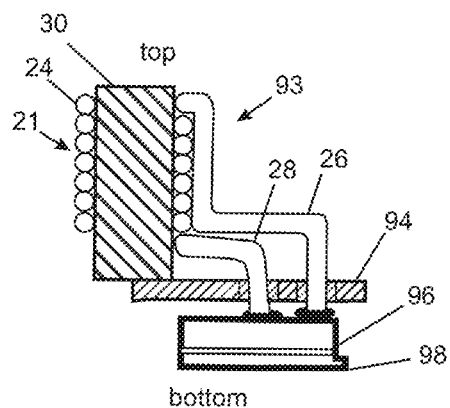
FIG. 13 shows a cross section of an embodiment of the invention where the magnetic field antenna is asymmetric.

An embodiment of the invention shown in FIG. 13 employs a more asymmetric design, compared to the previous embodiments described. A solid magnetic core 30, is shifted off-center compared to a speaker 96. The speaker 96 has a speaker outlet 98 oriented on a side face rather than the bottom face of the speaker 96. The speaker case in this embodiment comprises a flat rectangular plate 94.

Figure 14:
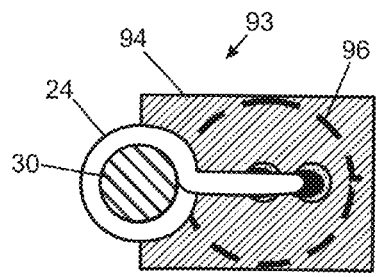
FIG. 14 shows a view the embodiment of the invention shown in FIG. 13 looking into the distal end of the embodiment.

A view into the distal end of this MFA 93 is seen in FIG. 14. From this view, the first turn 24 of the receiver coil 21 can be seen. The outline of the speaker 96 is shown as a dashed circle. From this view, the area defined by the first turn does not overlap with the area defined by the speaker 96 outline.

Figure 15:
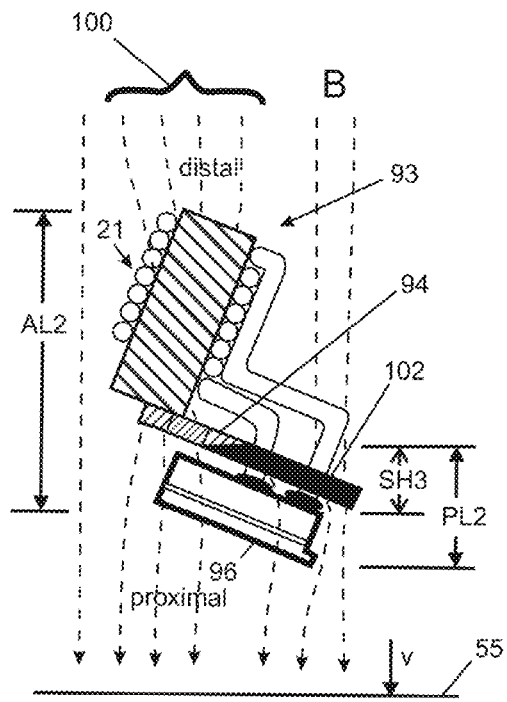
FIG. 15 shows a cross section of the embodiment of the invention from FIG. 13 where the magnetic field antenna is oriented relative to a magnetic field for maximum antenna coil voltage generation.

In FIG. 15, the MFA 93 from FIG. 13 and FIG. 14 is shown oriented to yield maximum sensitivity in a far field magnetic field. Because of the asymmetric geometry, the MFA 93 yields highest sensitivity when slightly rotated relative to the field vector v. The redirected field lines that pass through at least some of the turns of the coil 21 are indicated by label 100.

The effective MFA length is indicated by AL2. It can be seen that the speaker case 94 adds to this length when the MFA 93 is rotated in the field. The speaker case 94 provides a magnetic shunt 102 that redirects at least one field line around the speaker 96, the speaker 96 being a coupled electrical component. The effective magnetic shunt length is indicated by SH3 while the effective speaker length (effective part length) is indicated by PL2. The effective magnetic shunt length SH3 is shorter than the effective speaker length PL2, but still provides the benefit of increased effective MFA length AL2 and some shielding. An effective magnetic shunt length to effective part length ratio of a coupled electrical component, for example in this embodiment SH3/PL2, of at least 1/10 is desired to achieve redirection of the magnetic field around a coupled electrical component.

A large test transmitter coil with multiple turns that has a radius ten times the maximum dimension of the MFA under test can be used to generate a field at its center that approximates a far field for easily determining the optimal antenna orientation relative to the field vector of a far field. The optimal magnetic antenna orientation may be determined by placing the MFA in the center of the test transmitter coil and rotating the MFA until the maximum antenna coil voltage is achieved. The orientation of the MFA relative to the center axis of the test transmitter coil is the orientation with maximum sensitivity.

Figure 16:
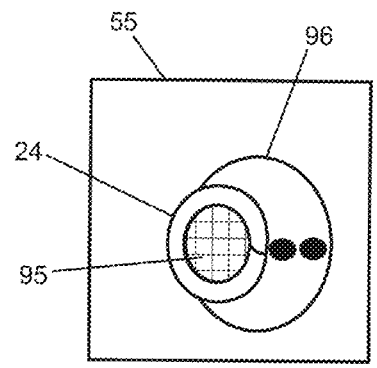
FIG. 16 shows the antenna coil and speaker of the embodiment of the invention from FIG. 13 projected onto the perpendicular field plane.

In FIG. 16, the first turn 24 and speaker 96 are projected into the perpendicular field plane 55. The areas defined by a projected first turn 95 and speaker 96 intersect in the region 95. Thus, when the MFA 93 is placed in a far field with optimal orientation with regard to sensitivity at least one turn of the coil 21 is "above" a coupled electrical component of the antenna. This geometry results in a receiver coil 21 and at least one coupled electrical component that are generally aligned along the unperturbed far field magnetic field path and enables an MFA 93 geometry that can result in a high sensitivity and provide shielding.

Figure 17:
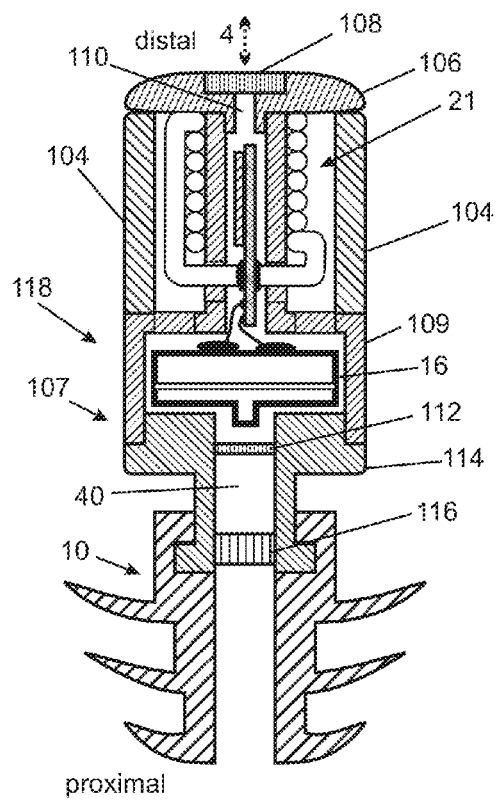
FIG. 17 shows a cross section of a preferred embodiment of the invention incorporating various additional components including a core cap made of magnetic material and an eartip adapter made of magnetic material.

FIG. 17 shows the cross section of another preferred embodiment of the invention as a wireless battery-free communications earplug 118. The communications earplug 118 has a similar exterior geometry to the embodiment shown in FIG. 1 in that it is symmetric about the earplug axis 4, employs a triple-flanged eartip 10 and is sized to fit in a human ear.

The MFA 78 from the embodiment shown in FIG. 10 is employed with an elongated section adjacent to the speaker 16 used to mechanically couple and attach a magnetic eartip adapter 114. The magnetic eartip adapter 114 is constructed using magnetic materials and is magnetically coupled to a single-piece magnetic core/extension 109, in this embodiment, because it is in close proximity with the magnetic core/extension 109 and is in contact with the magnetic core/extension 109. The antenna body 107, in this embodiment, comprises a magnetic cap 106, magnetic core/extension 109 and magnetic eartip adapter 114.

The magnetic cap 106 has a vent channel 110 for venting static pressure within the communications earplug 118 and distal end of speaker 16 and is magnetically coupled to the core/extension 109. The magnetic cap 106 also has a filter 108 that may be made from screen, foam, a gas-permeable membrane or other materials that allow for air pressure equalization but prevent dirt and small objects from passing into the interior of the communications earplug 118.

Within the magnetic eartip adapter 114 is an acoustic damper 112 used to control acoustic standing waves and electro-mechanical resonances of the speaker 16. Also within the magnetic eartip adapter 114 is a wax guard 116 used to prevent human ear wax from damaging the speaker 16 and clogging the eartip adapter sound channel 40.

A mechanical barrier 104 protects the MFA 78 from damage and can be made from molded plastic, overmolded plastic, overmolded elastomer and many other materials.

In this embodiment, the antenna body 107 forms at least part of the exterior surface of the communications earplug, which can yield a communications earplug 118 of smaller size. When incorporating a core/extension 109 that employs a hollow interior, it is possible to position the speaker 16 at the distal end and the antenna coil 21 at the proximal end by rotating the core/extension 109 180 degrees, and modifying the magnetic eartip adapter 114 and magnetic cap 106. This places the speaker 16 in the core/extension 109 so that the sound travels through the interior of the core/extension 109.

Figure 18:
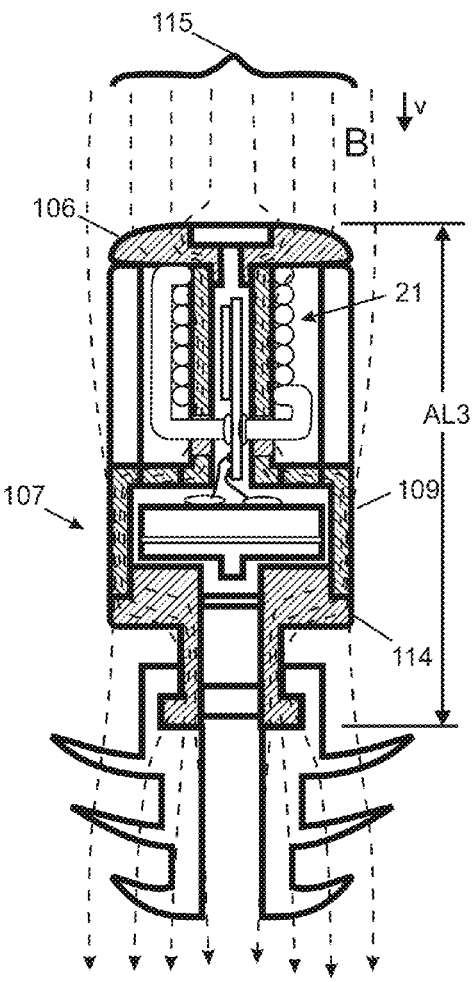
FIG. 18 shows a cross section of the preferred embodiment of the invention from FIG. 17 in a magnetic field illustrating the redirection of magnetic field lines.

In FIG. 18 the embodiment shown in FIG. 17 is shown in a magnetic far field. In FIG. 18 only the magnetic materials are indicated by hatching to indicate the magnetic antenna body 107. The effective length of the antenna body 107 is indicated by AL3.

It can be seen in this figure that constructing the eartip adapter 114 from magnetic material substantially increases the effective length of the antenna body 107. A magnetic eartip adapter can increase voltage sensitivity of a magnetic antenna by over 10%. This novel eartip adapter serves mechanical functions, acoustical functions and antenna functions simultaneously.

This embodiment of the invention yields a very effective magnetic shield and long effective length AL3 while remaining a compact size that can easily fit within an ear. This embodiment will redirect more magnetic field lines into the antenna coil 21 compared to the previously described embodiments, as indicated by field lines 115. To further improve sensitivity, a comfortable eartip 10 could be manufactured using impregnated magnetic materials.

Figure 19:
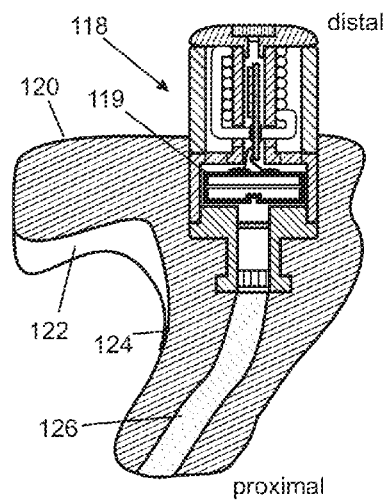
FIG. 19 shows a cross section of an embodiment of the invention using a custom-molded eartip.

When a user talks, speech can be detected as sound pressure changes in the users ear canals, especially when the canal is sealed with an earplug. FIG. 19 shows a cross section of an embodiment of the invention incorporating a custom-molded eartip 120 and a microphone 119 for sensing the sound pressure levels inside the ear canal of a user. The sensed sound pressure levels can be used for noise dosimetry purposes and/or for picking up speech communications from the user.

This custom-molded eartip 120 has a custom-molded canal section 124 and a custom-molded concha section 122. The custom-molded concha section 122 can be eliminated in some applications where only the custom-molded canal section 124 is required. A sound channel 126 through the custom-molded eartip 120 delivers sound from the ear canal to the microphone 119 of the MFA 118.

Figure 20:
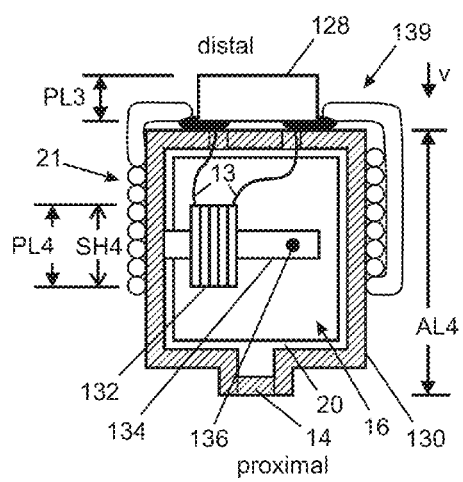
FIG. 20 shows a cross section of an embodiment of the invention where a single part functions as an antenna core and magnetic shunt.
Figure 21:
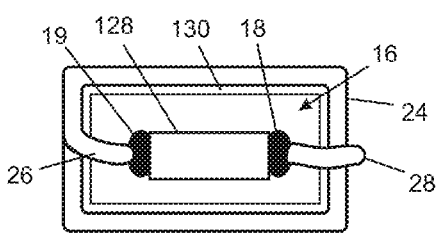
FIG. 21 shows a view an embodiment of the invention from FIG. 20 looking into the distal end of the magnetic field antenna.

FIG. 20 shows a cross-section of another embodiment of an MFA 139 while FIG. 21 shows the same embodiment looking into the distal end. This embodiment is oriented for maximum sensitivity along the far field field vector v. This embodiment comprises a speaker 16 where a magnetic speaker case 130 contains the speaker components: a speaker diaphragm 20, an armature coil 132, a diaphragm drive rod 136, and a cantilever beam 134 among other components not shown. In this embodiment three coupled electrical components are employed: the speaker resonator capacitor 128, armature coil 132 having effective lengths PL3 and PL4, respectively, and the armature leads 13. The armature coil 132 is electrically connected to the speaker terminals 18 and 19. A speaker resonator capacitor 128 is connected to the speaker terminals as are the ends 26 and 28 of the antenna coil 21. The speaker case 130 has a speaker output 14 where sound generated by the vibrating diaphragm 20 exits the speaker case 130.

The speaker case 130 in this embodiment is also the antenna body 130 and has effective antenna length of AL4. In this embodiment there are two magnetic shunt sections shunting the armature leads 13 and armature 132. The armature 132 shunt has length SH4. As seen in FIG. 21, the magnetic speaker case 130 in this embodiment can be rectangular, as can the antenna coil 21 and first turn 24. This embodiment of the invention could be imbedded in a custom-molded eartip without a separate eartip adapter or installed in a universal-fitting earplug shell for a wireless communications earplug, among other applications.

Figure 22:
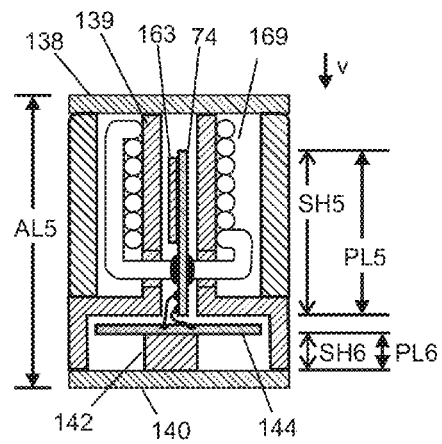
FIG. 22 shows a cross section of an embodiment of the invention incorporating active electronic components.

FIG. 22 shows an embodiment of the invention incorporating a circuit board 74, an active electronics circuit 163, a battery 142, and a circuit board for mounting the battery 144. In this embodiment, a transceiver coil 169 serves as both a receiver coil and a transmitter coil. This embodiment also incorporates a single-piece magnetic core/extension 139, a magnetic cap 138 and magnetic base 140. The battery 142 has an electrical influence on the transceiver 169 through the active electronics circuit 163 and is a coupled electrical component. The active electronics circuit 163 comprises multiple electronics components. This embodiment of the invention can be used in active radio frequency identification (RFID) systems and provides a compact form factor by incorporating a one-piece core/extension 139 with shielding properties.

The embodiment of FIG. 22 is shown oriented with respect to the far field field vector v for optimal sensitivity. In this embodiment, there are at least two shunt sections: one shunt section of length SH5 is shunting the circuit board 74 of length PL5, and therefore, shunting multiple coupled electrical components. Another shunt section of length SH6 is shunting the battery 142 with total part length PL6. In this embodiment, the antenna body comprises the magnetic cap 138, magnetic core/extension 139 and magnetic base 140. The total effective length of this antenna body is AL5.

Figure 23:
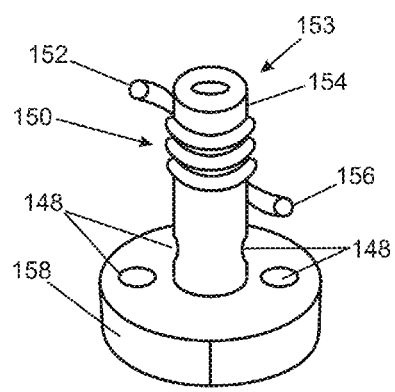
FIG. 23 shows a view of an embodiment of a magnetic field antenna body and antenna coil.

FIG. 23 shows an embodiment of an antenna body 153 with antenna coil 150. This embodiment of an antenna body employs cylindrical geometries and is constructed of a single piece of magnetic metal. This embodiment has a magnetic core 154 and magnetically coupled electronics case 158 that are formed from a single piece of magnetic metal. There are perforations 148 in the antenna body 153 so that the ends 152 and 156 of the coil 150 may be electrically connected to coupled electrical components (not shown) within the case 158. The magnetic core 154 and case 158 could be constructed from separate materials and bonded together, in another embodiment.

Figure 24:
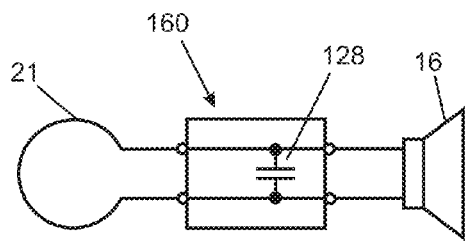
FIG. 24 is an electrical schematic of the embodiment of the invention shown of FIG. 20 and FIG. 21.

FIG. 24 is an electrical schematic for the embodiment shown in FIG. 20. The antenna coil 21 is electrically coupled to a passive electronics circuit 160 which is coupled to a speaker 16 that is a coupled electrical component. In this embodiment, the antenna coil 21 is a receiver coil for AF signals which drive speaker 16. The passive electronics circuit in this embodiment is a speaker resonator capacitor 128. The speaker resonator capacitor can boost the output of the speaker at higher audio frequencies, such as between 3 kHz and 20 kHz when selected properly, for improved speech intelligibility. The capacitor may be determined from using circuit simulator software or preferably by using a variable capacitor in the laboratory and varying the capacitance until the desired response is achieved, among other methods. The speaker resonator capacitor 128 also provides an additional benefit in that it filters higher frequencies, above the region where boosting occurs, such as radio frequencies which could cause spurious sounds if unfiltered. The speaker resonator capacitor 128 is connected in parallel with the coil 21 and speaker 16 in this embodiment.

Figure 25:
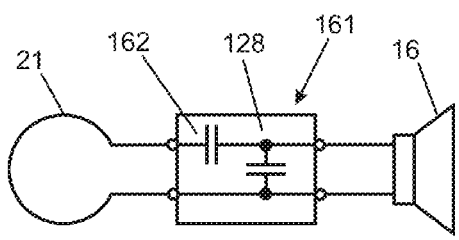
FIG. 25 is an electrical schematic of an embodiment of the invention incorporating a coupling capacitor and speaker resonator capacitor.

FIG. 25 shows an alternative embodiment of a passive electronics circuit 161 used in an embodiment of the invention. The addition of a coupling capacitor 162 attenuates low frequencies received by antenna coil 21 from being input to the speaker 16, while passing the desired AF signal on to the speaker 16. Sometimes it is desirable to attenuate frequencies below approximately 300 Hz to improve speech intelligibility if there are spurious low frequency signals present in the communications signal or picked up from stray magnetic fields. A speaker resonator capacitor 128 is also used in this embodiment to boost the high frequency output of the speaker 16, as discussed above with reference to FIG. 24.

Figure 26:
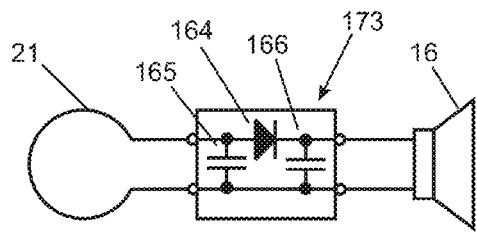
FIG. 26 is an electrical schematic of an embodiment of the invention incorporating an amplitude demodulator.

FIG. 26 shows another alternative embodiment of a passive electronics circuit 173 used in an embodiment of the invention. The passive electronics circuit 173 in this embodiment comprises an amplitude demodulation (AM) circuit. In this embodiment, the antenna coil 21 is a receiver coil and is now connected to a coil resonator capacitor 165. An AM magnetic field is generated by modulating an RF carrier signal with an AF communications signal, as is known in the art. The coil resonator capacitor 165 is selected to cause resonance at the frequency of the carrier signal. This selectively tunes the device to minimize interference from other frequencies and improves reception sensitivity at the desired frequencies.

This signal is rectified by rectifier diode 164 which is then filtered by filter capacitor 166 to remove higher frequencies that are outside of the audio frequency communication signal bandwidth in order to recover the original audio frequency communications signal, to the extent possible, as is common in the art. The filtered signal is input to the speaker 16. The embodiment of this circuit could be used in a wireless battery-free communications earplug employing the AM technique. The circuit 173 is considered passive here because it does not require an additional DC current or DC voltage source to provide power for its intended function.

Figure 27:
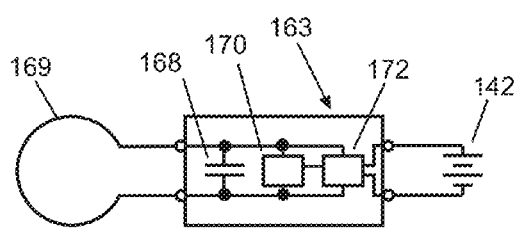
FIG. 27 is an electrical schematic of an embodiment of the invention shown in FIG. 22 incorporating an antenna coil resonator capacitor, modulator and variable impedance device.

FIG. 27 is a schematic of the embodiment shown in FIG. 22. The antenna coil 169 is a transceiver coil and is connected to a coil resonator capacitor 168 that creates a resonance with the transceiver coil and other circuits used in the embodiment where the resonance frequency generally corresponds to the center of the bandwidth of the frequencies of the magnetic field. A variable impedance device 170 can modulate the impedance "seen" by the transceiver coil 169. Active electronics 172 can comprise memory chips and microcontrollers as well as other active electronics for communicating with a remote system. The battery 142 provides DC voltage and current for the active electronics 172. This circuit, along with circuits known to the art, can be used as a radio frequency identification (RFID) device.

Figure 28:
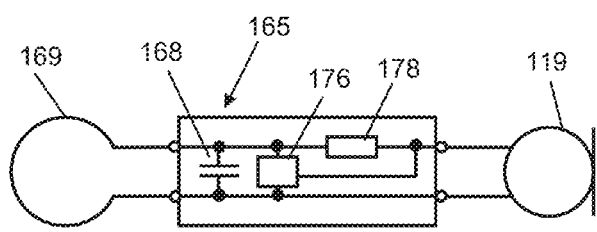
FIG. 28 is an electrical a schematic of an embodiment of the invention incorporating a microphone for sensing sound pressure levels in an ear canal.

FIG. 28 is a schematic of the embodiment of the invention shown in FIG. 19. In this embodiment, a microphone 119 is included, which is an active electrical component used to sense the sound pressure level in a user's ear canal. The microphone 119 is electrically connected to an electronics circuit 165. A carrier signal is sensed by the antenna coil 169, which functions as a transceiver coil, and a coil resonator capacitor 168 is used to tune the antenna to the fundamental frequency of the carrier. A variable load circuit 176 is capable of varying the electrical load "seen" by the transceiver as a function of the microphone 119 electrical output signal. A bias circuit 178 creates a DC voltage from a received transceiver signal to power the microphone 119 for proper operation of the microphone 119.

Using these components, and other circuits known in the art, the microphone 119 can cause variations in the electrical impedance "seen" by the coil 169, and this signal is re-radiated back through the transceiver coil 169 for pickup by a remote wireless receiver. The signal generated by the remote transmitter may be a pulsed signal, as in this embodiment, where the re-radiated signal generated by the MFA is picked up by a remote receiver during the periods when the remote transmitter is not transmitting signal, as is done in the art. Other circuits in additional embodiments could be employed to make use of a microphone 119 incorporated into the invention.

DEFINITIONS

A "Receiver" is a receiver coil along with any magnetic material used as a core within the internal region of the receiver coil. Magnetic material outside the region of an antenna coil and in close proximity to the core, preferably in mechanical contact with the core, may be called a "core extension".

An "electrical component" is a component that relies on the flow of electrical current and/or voltage in order to serve its function.

A "coupled electrical component" is an electrical component which, if removed, would affect the electrical current through the antenna coil and/or voltage at the ends of the antenna coil. The ends of an antenna coil may be electrically coupled to electrical components in applications for various purposes including generating sound, sensing sound, sensing acceleration, and sending/receiving digital information, among many other purposes. Thus, coupled electrical components are considered herein to be part of an MFA. Coupled electrical components may be "directly coupled" to the antenna coil, where at least one end of the coil has a very low impedance path to the electrical component, for example using a wire, or "indirectly coupled" to the antenna coil, where the ends of the coil are not connected through a low impedance path to the electrical component.

"Electronic components" are a subset of electrical components and include "passive" electronic components (for example, resistors, capacitors, inductors and some diodes among other components) and "active" electronic components (for example, discrete solid-state components such as most transistors and some diodes, or integrated circuits such as operational amplifiers, memory chips, digital signal processors and microcontrollers, among others). As a more general definition as used herein, "passive electronic components" are those that require no battery or other direct current (DC) voltage source or DC current source to provide power for the component to provide its intended function, while "active electronic components" require a battery or other direct current (DC) voltage or current source to provide power for the component to provide its intended function.

When an antenna coil is used to generate a voltage from an ambient magnetic field it is called a "receiver coil". When a coil is used to generate a magnetic field for reception by a remote device it is called a "transmitter coil". A "transceiver coil" is a coil that is used for both transmitting and receiving magnetic fields.

"AF" or "Audio Frequency" refers to the range of frequencies which are audible to the human ear, generally accepted as between roughly 20 Hz and 20,000 Hz (20 kHz), although it will be understood that this varies among individuals and changes as an individual ages. The speech band is a subset of this range and is often defined as being between 300 Hz and 3,400 Hz (3.4 kHz) in telephony (communications) purposes, which is generally considered adequate for intelligibility of signals, although higher frequency sound between 3 kHz and 20 kHz can be included to improve intelligibility if desired. As used herein, "AF signals" or "audio frequency signals" refers to signals in the frequency range of human hearing (either the full 20 Hz to 20 kHz range, or a subset of this range), which can be used to directly drive a transducer or speaker to produce sound without need for demodulation or detection of a carrier.

"RF" or "Radio Frequency" refers to AC frequencies above generally 50 kHz or higher. As used herein, "radio frequency signals" refers to signals which carry audible information by having the audio frequency information modulating an RF carrier signal, and from which the audio frequency information must be demodulated or detected by a demodulator to drive a transducer or speaker. This definition used herein may include magnetic signals with frequencies which are ultrasonic frequencies (for example 20 kHz-40 kHz), but which are modulated by the desired AF information and require demodulation in the receiver.

The "sensitivity" of an MFA refers to the ability of the antenna to convert a magnetic field into a useful purpose, such as generating sound.

As used herein, "magnetic material" means a material having a substantially lower reluctance compared to air, which provides an "easier" path for the magnetic field to travel through space. Magnetic material may be magnetized, as in the case of a permanent magnet, where the magnetic material generates a magnetic field on its own and is attracted to non-magnetized magnetic material. Magnetic material may also not be magnetized, where the magnetic material does not generate a magnetic field on its own and is not attracted to non-magnetized material. In one embodiment of the invention, an antenna body incorporating magnetized material can be beneficial if it is desired to attach the antenna to non-magnetized magnetic material or for other reasons. However, in many circumstances the use of magnetized material in the antenna body is detrimental because it can interfere with devices, such as compasses, and in another embodiment the antenna body does not incorporate magnetized magnetic material.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A magnetic field antenna comprising:
   a) an earplug body having a distal end and a proximal end;
   b) a magnetic core section within the earplug body;
   c) an antenna coil having at least one turn wrapped at least partially around the magnetic core section;
   d) at least one electrical component within the earplug body, electrically coupled to the antenna coil; and
   e) an eartip adapter at least partially made of magnetic material, located on the proximal end of the earplug body, the eartip adapter being magnetically coupled to the magnetic core section and acoustically coupled to the at least one electrical component.

2. The magnetic field antenna of claim 1, further comprising a magnetic shunt magnetically coupled to the magnetic core section and to the eartip adapter, at least partially magnetically shunting the at least one electrical component to provide at least partial magnetic shielding of the at least one electrical component.

3. The magnetic field antenna of claim 2, in which the earplug body has an outer surface comprising a cover adjacent the distal end of the earplug body and a base adjacent the proximal end of the earplug body, and the magnetic shunt forms at least part of the base.

4. The magnetic field antenna of claim 3, in which the magnetic core section and the magnetic shunt comprise a single part made of magnetic material.

5. The magnetic field antenna of claim 1, in which the antenna coil is located such that at least one turn of the antenna coil, projected into a perpendicular field axis plane, circumscribes an area that overlaps at least an area of the at least one electrical component projected onto the perpendicular field axis plane.

6. The magnetic field antenna of claim 1, in which the at least one electrical component comprises a speaker.

7. The magnetic field antenna of claim 1, in which the at least one electrical component comprises at least one passive electronic component.

8. The magnetic field antenna of claim 7, in which the passive electronic component comprises a capacitor connected in parallel with the antenna coil.

9. The magnetic field antenna of claim 1, in which the at least one electrical component comprises a microphone.

10. The magnetic field antenna of claim 1, further comprising a loop transmitter comprising a coil of wire.

11. The magnetic field antenna of claim 1, further comprising a molded eartip mounted on the eartip adapter.

12. A magnetic field antenna comprising:
    a) a body at least partially of magnetic material, having a distal end and a proximal end;
    b) a magnetic core section within the body adjacent to the distal end;
    c) an antenna coil having at least one turn wrapped at least partially around the magnetic core section; and
    d) at least one electrical component within the body, electrically coupled to the antenna coil;
    wherein the antenna coil is located such that at least one turn of the antenna coil, projected into a perpendicular field axis plane, circumscribes an area that overlaps at least an area of the at least one electrical component projected onto the perpendicular field axis plane.

13. The magnetic field antenna of claim 12, further comprising a magnetic shunt magnetically coupled to the magnetic core section, at least partially magnetically shunting the at least one electrical component to provide at least partial magnetic shielding of the at least one electrical component.

14. The magnetic field antenna of claim 13, in which the magnetic core section and the magnetic shunt comprise a single part made of magnetic material.

15. The magnetic field antenna of claim 13, in which the body has an outer surface and the magnetic shunt forms at least part of the outer surface.

16. The magnetic field antenna of claim 12, in which the at least one electrical component comprises a speaker.

17. The magnetic field antenna of claim 12, in which the at least one electrical component comprises at least one passive electronic component.

18. The magnetic field antenna of claim 17, in which the passive electronic component comprises a capacitor connected in parallel with the antenna coil.

19. The magnetic field antenna of claim 12, in which the at least one electrical component comprises a microphone.

20. The magnetic field antenna of claim 12, further comprising an eartip adapter on the proximal end of the body, acoustically coupled to the at least one electrical component.

21. The magnetic field antenna of claim 20, further comprising a molded eartip mounted on the eartip adapter.

22. A wireless earplug comprising:
    a) an earplug body having a distal end and a proximal end and an outer surface comprising a mechanical barrier adjacent the distal end of the earplug body and a base adjacent the proximal end of the earplug body;

b) a magnetic core section within the earplug body inside the mechanical barrier;
c) an antenna coil having at least one turn wrapped at least partially around the magnetic core section;
d) a speaker having a speaker output, located within the earplug body and electrically coupled to the antenna coil;
e) a magnetic shunt magnetically coupled to the magnetic core section, at least partially enclosing the speaker to provide at least partial magnetic shielding of the speaker; and
f) an eartip adapter at least partially made of magnetic material, located on the proximal end of the earplug body, the eartip adapter being magnetically coupled to the magnetic shunt and acoustically coupled to the speaker output.

23. The earplug of claim 22, in which the magnetic shunt forms at least part of the base.

24. The earplug of claim 22, further comprising a molded eartip mounted on the eartip adapter.

25. The earplug of claim 22, further comprising a loop transmitter comprising a coil of wire.

\* \* \* \* \*